United States Patent [19]

Van Savage et al.

[11] Patent Number: 5,545,442
[45] Date of Patent: Aug. 13, 1996

[54] METHOD FOR USING A RADIATION CURED DRUG RELEASE CONTROLLING MEMBRANE

[75] Inventors: Gary Van Savage, Bridgewater; James M. Clevenger, Glen Gardner, both of N.J.

[73] Assignee: Ciba-Geigy Corporation, Tarrytown, N.Y.

[21] Appl. No.: 463,473

[22] Filed: Jun. 5, 1995

Related U.S. Application Data

[62] Division of Ser. No. 238,115, May 4, 1994.

[51] Int. Cl.$^6$ .......................................................... C08J 7/04
[52] U.S. Cl. ............................. 427/513; 522/50; 522/86; 522/88; 522/153; 522/154; 424/422; 424/443; 424/499; 427/517
[58] Field of Search ...................................... 427/513, 517; 522/50, 86, 88, 153, 154; 424/499, 422, 443

[56] References Cited

U.S. PATENT DOCUMENTS

| Re. 27,401 | 6/1972 | Wichterle et al. |
|---|---|---|
| 2,976,576 | 3/1961 | Wichterle et al. |
| 3,077,468 | 2/1963 | Gearden |
| 3,220,960 | 11/1965 | Wichterle |
| 3,272,640 | 9/1966 | Geurden |
| 3,520,949 | 7/1970 | Shepherd et al. |
| 4,192,827 | 3/1980 | Mueller et al. |
| 4,277,582 | 7/1981 | Mueller et al. |
| 4,745,042 | 5/1988 | Sasago et al. ............................ 522/88 |
| 4,778,880 | 10/1988 | Symes et al. ............................. 522/88 |

FOREIGN PATENT DOCUMENTS

| 54-128482 | 10/1979 | Japan ....................................... 522/88 |
|---|---|---|
| 9309176 | 3/1993 | WIPO . |

OTHER PUBLICATIONS

Uehara et al; Makuzai Gakkaishi vol. 36, No. 6 pp. 448–453 (1990) Effect of Corena Discharge Treatment on Hydroxyethyl Cellulose.
Natural Product Literature by Aqualon Physical and Chemical Properties, 1987.
Kirk Othmer: Encyclopedia of Chem. Tech. 3rd. Ed. J. Wiley & Sons (N.Y.) pp. 108–121.
Ishikawa et al. Chem. Pharm Bull 41(9) 1626–1631 (1993).
Merck Index 10th Ed. Entry 8099 Riboflavin.
Translation of JP 54–128482.

*Primary Examiner*—Mark Chapman
*Attorney, Agent, or Firm*—Luther A. R. Hall

[57] ABSTRACT

This invention pertains to cross-linked hydrophilic polymeric films, the process of making such films, and their use. The films of this invention are produced by solubilizing a water-soluble polymer with a photosensitive or light degradable catalyst, optionally drying said solution, and exposing the solution to an energy source, particularly light. These films are suitable for use as a carrier for biologically active agents, such as pharmaceuticals, both human and veterinary, insecticides, and fertilizers; as hydrophilic membranes for separation processes; as bandages for wound treatment; as body implants or as coatings for such implants; and as coatings on glass, metal, wood or ceramics.

8 Claims, No Drawings

METHOD FOR USING A RADIATION CURED DRUG RELEASE CONTROLLING MEMBRANE

This is a divisional of Ser. No. 08/238,115 filed May 4,1994.

BACKGROUND OF THE INVENTION

This invention relates to cross-linked hydrophilic polymeric films, the process of making such films, and their use in applications where strength of the polymer article and high permeability to water are required simultaneously. In particular, these films are suitable for use as a carrier for biologically active agents, such as pharmaceuticals, both human and veterinary, insecticides, and fertilizers; as hydrophilic membranes for separation processes; as bandages for wound treatment; as body implants or as coatings for such implants; and as coatings on glass, metal, wood or ceramics.

Such films, particularly when used as biological carriers, should not only be able to entrap the biological agent, but should also be biocompatible; that is, both mild and non-cytotoxic to living organisms. Additionally, they should be chemically and mechanically stable.

Cross-linked polymeric films have been made. For example, U.S. Pat. Nos. 2,976,576 and 3,220,960 disclose cross-linked hydrophilic polymers which are produced by polymerizing a hydrophilic monomer in the presence of a cross-linking agent; U.S. Pat. No. 3,520,94 discloses hydrophilic cross-linked polymers which are produced by admixing a water-soluble polymerizable hydroxyalkyl monoester of a mono-olefinic monocarboxylic acid and a polymerizable diester of a mono-olefinic monocarboxylic acid in the presence of a linear polyamide; and U.S. Pat. Nos. 4,192,827 and 4,277,582 disclose cross-linked polymers which are produced from a polymer of mono-olefinic monomers or copolymer of mono-olefinic monomers which is cross-linked with a terminal diolefinic hydrophobic macromer. However, the use of monomers is disadvantageous in the pharmaceutical industry due to the potential cytotoxicity of unreacted monomers.

Other cross-linked polymeric films have been made from polymers, thereby overcoming the problem of unreacted monomers. For example. WO 93/09176 discloses cross-linking of polysaccharides, polycations and lipids with polymerizable acrylate in the presence of a radical initiator by using certain sources of energy; U.S. Pat. No. 3,077,468 discloses the method of cross-linking water-soluble hydroxyalkyl polysaccharide ethers by reacting them with an insolubilizing agent selected from unsaturated dibasic aliphatic acids and their anhydrides and the water-soluble derivatives of said acids and their anhydrides; and U.S. Pat. No. 3,272,640 discloses cross-linking water-soluble polymers by reacting them with a hydrophobic film former.

SUMMARY OF THE INVENTION

It is accordingly an object to the present invention to provide cross-linked, hydrophilic polymeric films which are suitable for use as a carrier for biologically active agents, such as pharmaceuticals, both human and veterinary, insecticides, and fertilizers; as hydrophilic membranes for separation processes; as bandages for wound treatment; as body implants or as coatings for such implants; and as coatings on glass, metal, wood or ceramics.

It is another object of this invention to provide such a film which is essentially insoluble in aqueous and non-aqueous solutions.

It is yet another object of this invention to provide a cross-linked hydrophilic polymeric film which can be prepared without the use of organic solvents.

It is still another object of this invention to provide a cross-linked hydrophilic polymeric film which is safe for in vivo usage.

These, and other objects apparent to those skilled in the art from the following detailed description, are accomplished by the present invention which pertains to cross-linked hydrophilic polymeric films, the process of making such films, and their use. These films are produced by the application of an aqueous solution of a water-soluble polymer and a photosensitive or light degradable catalyst to a suitable substrate, optionally drying said solution, and exposing the resultant film to a suitably interacting energy source.

DETAILED DESCRIPTION OF THE INVENTION

This invention pertains to cross-linked hydrophilic polymeric films, the process of making such films, and their use. These film are produced by the application of an aqueous solution of a water-soluble polymer and a photosensitive or light degradable catalyst to a suitable substrate, optionally drying said solution, and exposing the resultant film to a suitably interacting energy source.

Appropriate polymers are those which are water-soluble and possess a structure which, in the presence of a suitable catalyst or cross-linking agent, may bond to additional molecules, thus yielding a macromolecule of said polymer which, due to its increased molecular weight, is no longer readily soluble in an aqueous medium. These polymers include, but are not limited to, water-soluble polyvinyl alcohols, poly(hydroxyethyl methacrylates), and polysaccharides, particularly hydroxyalkyl polysaccharide ethers, more particularly cellulose ethers such as hydroxyethyl cellulose and hydroxpropyl methylcellulose. Polymers which have low viscosities are preferred; those which have viscosities which approach that of water are most preferred.

The amount of polymer used is that which can be solubilized in water and still remains free-flowing. A solution with a viscosity near that of water is preferred. Particularly, from about 1.0 to about 30% (w/w), more particularly from about 1.0 to about 6.0% (w/w) of the polymer is used.

Appropriate catalysts include those which are photosensitive or light degradable, such as azo dyes and riboflavin. The catalysts include, but are not limited to, riboflavin and its derivatives, Congo red, Evans blue, chlorazodin, erythrosine (FD&C Red #3), FD&C Red #40, tartrazine (FD&C Yellow #5), fast green FCF (FD&C Green #3), sunset yellow FCF (FD&C Yellow #6), brilliant blue FCF (FD&C Blue #1), and indigotine (FD&C Blue #2). In particular, the catalyst is a flavin. More particularly, the catalyst is riboflavin or a riboflavin derivative, preferably water soluble riboflavin derivatives, including, but not limited to, riboflavin-5'-phosphate or a salt thereof, riboflavin-5'-adenosine diphosphate, 6-hydroxyriboflavin, 8-nor-8-hydroxyriboflavin, roseoflavin, 5-deazariboflavin, 8α-($N^1$-histidyl)flavin, 8α-($N^3$-histidyl)flavin, 8α-S-cysteinylflavin, 6-S-cysteinylflavin, lumiflavin, and lumichrome. Most particularly the catalyst is riboflavin-5'-phosphate sodium.

Typically 0.1 to 10% (w/w), more particularly from about 1.0 to about 4% (w/w) of the catalyst is used, based on the total weight of the solids (polymer plus catalyst) in solution.

Before forming the film, the solution of polymer plus catalyst may be deaerated so as to decrease the amount of air trapped within the final product. Deaeration may be accomplished by allowing the solution to stand, particularly in a darkened, refrigerated room, ie. overnight, or by conventional methods known in the art. Although it is not necessary, deaeration generally improves the quality of the resultant film.

To form the film, the polymer is applied to a substrate. If the film is to be formed separately, as opposed to being coated onto an object, the substrate should be a smooth, non-reactive surface, ie. glass. Application may be by any conventional method known in the art.

The film is preferably allowed to dry before exposure to the energy source. Although this will occur at ambient temperatures, heat and or vacuum may be applied to decrease drying time. The film is preferably allowed to dry to a water content of no more than 30%, more narrowly to one of no more than 10%. However, as the film is hydrophilic, it is common for it to pick up water, thus rehydrating to some extent.

The energy source used to cure the polymer may be any type of electromagnetic radiation, such as actinic light, x-rays, or gamma radiation. Light sources, particularly those within the ultraviolet or visible range, are preferred, particularly those with wavelengths of from approximately 200 to approximately 800 nanometers, more particularly those with wavelengths of from approximately 300 to approximately 700 nanometers. When the polymer is to be used as a carrier for a biologically active agent, particularly pharmaceuticals, it has been found that light within the visible range is most preferred because of the potential for degradation of the active agent outside of this range. The wavelength most suited to use in any particular curing will depend upon the catalyst chosen.

The film should be exposed to the energy source for such time as is necessary to achieve the desired amount of cross-linking of the polymer, particularly for such time as is necessary to ensure that the film is no longer freely soluble in an aqueous medium. The exposure time is dependent upon the intensity and type of energy source used as well as the type of polymer and thickness of the film. Sufficient exposure is generally indicated by a change in film color due to the catalyst. For example, the film turns from a bright yellow to a yellow-brown color when riboflavin or a derivative thereof is used as the catalyst.

Surprisingly, the instant reaction will occur in the presence of oxygen unlike many others in which free radical scavenging inhibits the reaction. In addition, when the energy source used is light, the reaction is substantially temperature independent within the range of 0°–100° C. though ambient conditions are considered to be best.

The reaction may proceed without organic solvents. Whenever organic solvents are used in a pharmaceutical process, measures need to be taken to protect the operators who produce the dosage forms and the environment from overexposure to the hazardous, often teratogenic and carcinogenic, materials. Additional precautions are necessary to protect equipment and facilities from harm. Further, despite all precautions, it is still likely for detectable levels of residual solvent to remain in the finished dosage form. Not only is the instant process advantageously safer, but the resultant film is safer in that it does not contain residual organic solvents. Thus, the present reaction, which may proceed without organic solvents, is advantageous, especially in the pharmaceutical industry.

Another safety advantage in the pharmaceutical industry is that since polymeric, not monomeric, materials are used, the cytotoxic potential of unreacted monomers is eliminated. Further, the film may be made with ingredients which are "generally regarded as safe" (GRAS) by the Food and Drug Administration.

The cured polymer may be applied using any conventional coating technique including, but not limited to, spray coating, dip coating, and fluidized bed coating.

The resultant film is substantially water insoluble and hydrophilic. Further, it tends to be insoluble in both acidic and alkaline solutions. The film is not appreciably elastic, but is flexible and continuous.

The possible film thickness is dependent upon the light penetration. If thicker films are desired, however, multiple layers may be applied successively, each layer being cured before the next layer is deposited. This is especially useful in coating processes, for example coating of a pharmaceutical dosage form.

The resultant film can be used, inter alia, as a carrier for biologically active agents, particularly pharmaceutically active agents. The term "pharmaceutically active agent," as used herein, refers to any composition of matter which will produce a pharmacological or biological response, including pharmaceuticals which are used to treat the body topically as well as systemically. Suitable mixtures of such active agents can be dispensed with equal facility as with single component systems. Furthermore, derivatives of these pharmaceutically active agents, eg. ethers, esters, amides, etc., which are easily hydrolyzed within the body can be employed as can various forms of the active agents, eg. salts, acids, complexes, etc.

Pharmaceutically active agents useful in the present invention include, but are not limited to, proteins and peptides, antiasthmatics, antianginals, corticosteroids, 5-lipoxygenase inhibitors, antihypertensives, and leukotriene B4 receptor antagonists. Proteins and peptides include, but are not limited to, transforming growth factors (TGF), immunoglobulin E (IgE) binding factors, interleukins, interferons (IFN), insulin-like growth factors (IGF), milk growth factors, anticoagulants, anabolics, analgesics, androgens, antibiotics, androgens, antidepressants, antidiabetics, anticonvulsants, antihistamines, antihypertensives, antiinfectives, antiparasistics, antiparkinson agents, antiphlogistics, antitussives, appetite depressants, bronchodilators, coronary dilators, corticoids, cytostatics, diuretics, hypnotics, neuroleptics, psycho-analeptics, tranquilizers, uricosurics, vasodilators, and parathyroid hormones (PTH). Specific active agents include, but are not limited to IGF-I, PTH (1–34) and analogues thereof, $TGF_\alpha$, $TGF_{\beta1}$, $TGF_{\beta2}$, $TGF_{\beta3}$, $IFN_\alpha$, hybrid $IFN_\alpha$, $IFN_\gamma$, hirudin, heparin, calcitonin, 5-aminosalicyclic acid, CGS 23885, CGS 25019C, CGS 26529, Zileuton, ONO-LB 457, beclomethasone dipropionate, betamethasone-17-valerate, prednisolone metasulfobenzoate, tixocortol pivalate, budesonide, fluticasone, metoprolol fumarate, metoprolol tartrate, tetrahydroaminoacridine (THA), galanthamine, theophylline, ursodiol, clomipramine hydrochloride, terbutaline sulfate, aminoglutethimide, deferoxamine mesylate, estradiol, isoniazid, metyrapone, methandrostenolone, acetylsalicylic acid, phenylbutazone, methadone, methyltestosterone, imipramine, maprotiline, phenformin, carbamazepine, tripelennamine, hydralazine, trimethoprim, nifurtimox, levodopa, naproxen, benzonatate, mazindol, fenoterol, fenalcomine, dexamethasone, floxuridine, hydrochlorothizide, glutethimide, reserpine, methylphenidate, diazepam, sulfinpyrazone, isoproterenol, and rifampin.

As used herein, the active agents CGS 23885, 25019C, CGS 26529, Zileuton, ONO-LB 457 are defined as follows: CGS 23885 refers to N-hydroxy-N-((6-phenoxy -2H-1-benzopyran-3-yl)methyl)-urea; CGS 25019C refers to 4-[5-[4-(aminoiminomethyl)-phenoxy]pentoxy]-3-methoxy-N,N-bis(1-methylethyl)benzamide(Z)-2-butenedioate; CGS 26529 refers to N-[2-[[2-[[4-(4-fluorophenyl)phenyl]methyl]-1,2,3,4-tetrahydro-1-oxo-6 -isoquinolinyl]oxy]ethyl]-N-hydroxyurea; Zileuton refers to 1-(1-benzo[b]thien-2-yl-ethyl)-1-hydroxyurea; ONO-LB 457 refers to 5-[2-(2-carboxyethyl)-3-{6-(para-methoxyphenyl)- 5E-hexenyl}-oxyphenoxy]valeric acid.

Incorporation of the biologically active agent into the polymeric film may be accomplished by dissolution or dispersion into the polymer solution prior to curing or by diffusion into the finished article after cross-linking has occurred. In the alternative, the polymeric film can be hydrated in a solution of the active agent to be delivered and the solvent is then evaporated, leaving the agent within the film.

The biologically active agent may also be incorporated by techniques known in the art, for example microcapsules could be formulated by air-jet droplet generation, co-axial extrusion, or by emulsification. Incorporation may also be accomplished by coating the agent, either alone or admixed with acceptable excipients, using coating techniques known in the art, for example spray-coating or fluidized bed coating.

A pharmaceutical dosage form, such as a tablet or capsule, may alternatively be coated by admixing the polymer and catalyst, compression coating said mixture onto the pharmaceutical dosage form, and then exposing the compression coated form to the energy source. In this manner, the film is formed without any solvents. Techniques known in the art may be used to optimize this process; for example, the polymer/catalyst mixture may be ground to an appropriate particle size or acceptable tabletting agents may be added to the mixture.

The amount of the biologically active agent incorporated within the film may vary widely depending upon the particular agent, the desired therapeutic effect, and the time span of release.

As a carrier, the film may be used as a semi-permeable membrane for controlled release delivery systems. The film may be used to coat products for controlled sustained release of their contents as is or the coated product may be further outfitted with an orifice for release of active agent. In this latter embodiment, the coated product functions in a manner similar to those utilizing the oral osmotic technology known under the Alza tradename OROS®. This product permits passage of water and certain dissolved materials, but retains others, thus allowing active agent to be emitted at a controlled rate. The films of this invention however differ from the typical semipermeable membrane used in an OROS-type system in that a release orifice is optional, not necessary.

An additional advantage is that these polymeric films are easily removable before cross-linking as the polymer will readily form a viscous gel upon exposure to humidified environments. The gel-like film can then be easily removed by mechanical intervention. This is especially important in the field of pharmaceuticals as the film can be separated from the active agent after the delivery device has been made. This separation allows for recovery of expensive pharmaceutical active agents.

EXAMPLES

Example 1

2% (w/w) Hydroxyethylcellulose with a viscosity averaged molecular weight of 720,000 and 0.031% (w/w based on total solids) riboflavin-5'-phosphate are dissolved in distilled water. The resultant solution is allowed to deaerate in a dark refrigerator overnight. The deaerated solution is poured onto a glass plate and spread to a thickness of 12 mils (0.305 mm) and subsequently dried in a conventional oven at 50° C. to a moisture content of less than 10%. The film is then exposed to a visible light source rated at 600 footcandles (Hotpack environmental cabinet) for twenty-four hours. The resultant film is greater than 90% insoluble in water at ambient conditions.

Example 2

Three grams of hydroxyethylcellulose with a viscosity averaged molecular weight of 90,000 and a degree of substitution of 2.5 (ie. Natrosol 250L) and 60 mg of FD&C Blue #2 are dissolved in 100 ml of distilled water. The resultant solution is poured onto glass plates and spread to a thickness of 12 mils (0.305 mm) and subsequently dried in a conventional oven at 50° C. to a moisture content of less than 10%. The film is then exposed to a high intensity ultraviolet lightsource (Mercury "H" bulb, 600 Watts/inch) for approximately 30 seconds. The resultant film is crosslinked and is insoluble, but swellable in water.

Example 3

The process of Example 2 is repeated with the exception that the catalyst used is riboflavin-5'-phosphate.

Example 4

2% (w/w) Hydroxyethylcellulose with a viscosity averaged molecular weight of 720,000 and a degree of substitution of 2.5 (grade M) and 2% (w/w based on total solids) riboflavin-5'-phosphate are dissolved in distilled water using a homogenizer. The resultant solution is deaerated overnight in a dark refrigerator. The deaerated solution is poured onto a glass plate which had been preheated to 60° C. and spread to a wet thickness of 0.040 inches (approximately 1.0 mm). The film is subsequently dried in a conventional oven at 60° C. overnight. The film is then exposed to a high intensity ultraviolet lightsource (Mercury "H" bulb, 600 Watts/inch) for 30 seconds. The resultant film is approximately 75% insoluble in water at ambient conditions.

Example 5

The process of Example 4 is repeated with the exception that the energy source used is visible light rated at 600 footcandles (Hotpack environmental cabinet) and exposure is for twenty-four hours. The resultant film is in excess of 80% insoluble in water at ambient conditions.

Example 6

1.5% (w/w) Hydroxyethylcellulose which has a viscosity averaged molecular weight of 720,000 and a degree of substitution of 2.5 (Natrosol 250M) and 0.031% (w/w) riboflavin-5'-phosphate are dissolved in distilled water using a conventional mixer. The solution is deaerated overnight in a darkened refrigerator.

10.5 Kg of this solution is used to coat 1.25 Kg of 75 mg tablets containing dextromethorphan using conventional spraying in a pharmaceutical coating pan. The resultant coated tablets each contain 6.1 mg coating.

Example 7

The process of Example 6 is repeated except that the coated tablets are then exposed to ultraviolet light (Mercury "H" bulb, 600 Watts/inch) on all sides for approximately 60 seconds.

Example 8

A standard USP dissolution test in water USP is used to compare the coated tablets of Examples 6 and 7. Exposure of the coated tablets to ultraviolet light significantly decreased the dissolution rate. Eighty percent release occurred at 30 minutes for the tablets of Example 6, but did not occur until 150 minutes for the tablets of Example 7, a five-fold difference.

Example 9

The process of Example 7 is repeated except that the coating weight of each tablet is 7.9 mg and the energy source is visible light rated at 600 footcandles (Hotpack environmental cabinet) with exposure for 7 days.

Example 10

The process of Example 9 is repeated except that each tablet is pierced with a single hole measuring 0.025 inches (approximately 0.635 mm) in diameter to form a release orifice.

Example 11

A standard USP dissolution test in water USP is used to compare the coated tablets of Examples 9 and 10. Eighty percent release occurred at 3 hours for the tablets of Example 9, but did not occur until 4.1 hours for the tablets of Example 10.

Example 12

1.5% (w/w) Hydroxyethylcellulose which has a viscosity averaged molecular weight of 720,000 and a degree of substitution of 2.5 (Natrosol 250M) and 0.031% (w/w) riboflavin-5'-phosphate are dissolved in distilled water using a conventional mixer. The solution is deaerated overnight in a darkened refrigerator.

10.5 Kg of this solution is used to coat 1.25 Kg of 215 mg tablets containing metoprolol fumarate using conventional spraying in a pharmaceutical coating pan. The resultant coated tablets each contain 18 mg coating.

Example 13

The process of Example 12 is repeated except the coated tablets were exposed to 600 foot-candles of visible light for 6 days.

Example 14

A standard USP dissolution test in water USP is used to compare the coated tablets of Examples 12 and 13. Eighty percent release occurred at 3 hours for the tablets of Example 13, but did not occur until 6 hours for the tablets of Example 12.

The above description is for the purpose of teaching the person of ordinary skill in the art how to practice the present invention and it is not intended to detail all those obvious modifications and variations of it which will become apparent to the skilled worker upon reading the description. It is intended, however, that all such obvious modifications and variations be included within the scope of the present invention and by the following claims.

What is claimed is:

1. A method of coating a pharmaceutical dosage form with a hydrophilic cross-linked polymer which comprises admixing a water-soluble polymer consisting of hydroxyethyl cellulose or hydroxypropyl methyl cellulose and an effective amount of a photosensitive or light degradable catalyst to form a mixture;

compression coating said mixture over a pharmaceutical dosage form; and exposing the coated dosage form to an electromagnetic energy source.

2. A method according to claim 1 wherein the catalyst is selected from the group consisting of flavins, Congo red, Evans blue, chlorazodin, erythrosine (FD&C Red #3), FD&C Red #40, tartrazine (FD&C Yellow #5), fast green FCF (FD&C Green #3), sunset yellow FCF (FD&C Yellow #6), brilliant blue FCF (FD&C Blue #1) and indigotine (FD&C Blue #2).

3. A method according to claim 2 wherein the flavinoid catalyst is selected from the group consisting of riboflavin and riboflavin derivatives.

4. A method according to claim 2 wherein the flavinoid catalyst is riboflavin-5'-phosphate or a salt thereof.

5. A method according to claim 1 wherein the amount of catalyst used is from about 0.1 to about 10% of the combined weight of polymer and catalyst.

6. A method according to claim 1 wherein the energy source is light.

7. A method according to claim 6 wherein the light is visible or ultraviolet.

8. A method according to claim 7 wherein the light is in the range of from approximately 400 to approximately 700 nanometers.

* * * * *